(12) United States Patent
Komatsu et al.

(10) Patent No.: US 6,683,117 B2
(45) Date of Patent: Jan. 27, 2004

(54) OILINESS AGENT AND WATER-IN-OIL EMULSION CONTAINING SAME

(75) Inventors: Yoshinobu Komatsu, Tokyo (JP); Hitoshi Ishida, Tokyo (JP); Kouji Inoue, Tokyo (JP); Hiroshi Igarashi, Tokyo (JP); Masami Kondou, Tokyo (JP); Madoka Minagawa, Tokyo (JP); Tetsu Sato, Tokyo (JP); Hiroshi Ogawa, Tokyo (JP)

(73) Assignee: Mizusawa Industrial Chemicals Ltd, Tokyo (JP)

(*) Notice: Subject to any disclaimer, the term of this patent is extended or adjusted under 35 U.S.C. 154(b) by 0 days.

(21) Appl. No.: 10/056,016

(22) Filed: Jan. 28, 2002

(65) Prior Publication Data

US 2003/0045590 A1 Mar. 6, 2003

(30) Foreign Application Priority Data

Apr. 6, 2001 (JP) .......................... 2001-108572

(51) Int. Cl.$^7$ .................. B01F 17/00; B01J 13/00; C10M 129/40
(52) U.S. Cl. ................ 516/22; 508/381; 514/937; 516/100
(58) Field of Search ................ 516/22, 100; 514/937; 423/600; 554/76; 508/381

(56) References Cited

U.S. PATENT DOCUMENTS

| | | | | |
|---|---|---|---|---|
| 4,333,846 A | * | 6/1982 | Lee et al. ............... 423/600 X |
| 4,695,402 A | * | 9/1987 | Finlayson et al. ...... 516/100 X |
| 4,990,268 A | * | 2/1991 | Burba, III et al. ...... 423/600 X |
| 5,015,469 A | * | 5/1991 | Yoneyama et al. ....... 516/22 X |
| 5,142,077 A | * | 8/1992 | Martin et al. ............ 423/600 X |
| 5,169,967 A | * | 12/1992 | Assmus et al. ............ 554/76 X |
| 5,362,482 A | * | 11/1994 | Yoneyama et al. ...... 514/937 X |
| 5,443,761 A | * | 8/1995 | Burba, III et al. ............ 516/22 |
| 5,853,711 A | * | 12/1998 | Nakamura et al. ...... 514/937 X |
| 6,042,815 A | * | 3/2000 | Kellner et al. .......... 514/937 X |

* cited by examiner

Primary Examiner—Richard D. Lovering
(74) Attorney, Agent, or Firm—Sherman & Shalloway

(57) ABSTRACT

An oiliness agent comprising a carboxylate of a composite metal hydroxide having a chemical composition represented by the following general formula (1), $$M^2{}_a M^3{}_x (OH)_y (A)_z \cdot n H_2 O \qquad (1)$$

wherein, $M^2$ indicates a divalent metal, $M^3$ indicates a trivalent metal, A indicates an anion of an aliphatic carboxylic acid, a, x, y, and z are numbers satisfying the following formulas:

$a>0$, $3x+2a-y-mz=0$ (wherein m is a valency of anion A), $0.3 \leq a/x \leq 2.5$ $1.5 \leq y/(a+x) \leq 3.0$ $1.0 \leq (a+x)/z \leq 20.0$, and n is a number not larger than 7. The oiliness agent exhibits excellent emulsifying properties such as dispersion stability and moisture retaining property without emitting odor and without a tendency of being colored, and is very useful for forming a water-in-oil emulsion which can be effectively used as a base material for cosmetics.

19 Claims, 5 Drawing Sheets

OILINESS AGENT AND WATER-IN-OIL EMULSION CONTAINING SAME

BACKGROUND OF THE INVENTION

1. Field of the Invention

The present invention relates to a novel oiliness agent comprising a carboxylate of a layered crystalline composite metal hydroxide. More specifically, the invention relates to an oiliness agent useful as an emulsifier, as a thixotropy-imparting agent, as a viscosity-imparting agent and as a base material for cosmetics.

2. Description of the Prior Art

Emulsions can roughly be divided into two types; i.e., those of the oil-in-water (O/W) type and those of the water-in-oil (W/O) type. The former emulsions can be represented by a mayonnaise in which oil particles are dispersed in water, and the latter emulsions can be represented by a margarine or a butter in which water particles are dispersed in oil.

Among these emulsions, the O/W type emulsion in which a small amount of oil is dispersed in a large amount of water can be prepared relatively easily, but it is not necessarily easy to prepare the W/O type emulsion in which a large amount of water is dispersed in a small amount of oil.

As a known example of the water-in-oil type emulsion, Japanese Unexamined Patent Publication (Kokai) No. 81827/1982 discloses the one comprising a branched chain nonpolar oil, a nonionic liquid emulsifier, a reaction product of a sodium-magnesium-fluorotrisilicate-trioctahedral-montmorillonite-clay and a quaternary ammonium salt, a water-soluble magnesium salt and water, 75 to 98% by volume of the emulsion being of the aqueous phase, and 25 to 2% by volume of the emulsion being of the oil phase.

Further, Japanese Unexamined Patent Publication (Kokai) No. 151351/1988 discloses a water-in-oil type emulsified composition comprising, as essential components, a water-swelling clay mineral, a nonionic surfactant, an oil and water.

Japanese Unexamined Patent Publication (Kokai) No. 48228/1995 discloses a rouge composition comprising an organic modified clay mineral obtained by treating a water-swelling clay mineral with a quaternary ammonium-type cationic surfactant and a composite lipid or a nonionic surfactant, and an oil and a water-phase component.

However, the water-in-oil type emulsions taught in the above prior arts use a clay mineral in which the quaternary ammonium salt is incorporated among the layers as well as the nonionic surfactant. Besides, the organic clay mineral emits its particular odor, tends to be colored upon the passage of time, and stimulates the skin to a degree which is not negligible. Therefore, it has been desired to provide an emulsifier to substitute for the above emulsions.

In preparing the known water-in-oil type emulsions as pointed out already, much limitation is imposed on the surfactant, on the method of mechanical stirring, on the order of mixing, and on selecting various conditions such as temperature and the like.

Besides, most of the water-in-oil type emulsions that are formed are not still capable of satisfying the dispersion stability and the moisture retaining property to a satisfactory degree. It has therefore been eagerly desired to provide a water-in-oil type emulsion that can be easily prepared and that exhibits excellent dispersion stability and moisture retaining property.

SUMMARY OF THE INVENTION

It is therefore an object of the present invention to provide an oiliness agent which can be effectively used as an emulsifier for forming a water-in-oil type emulsion exhibiting excellent dispersion stability and moisture retaining property without emitting odor and without having a tendency of being colored.

Another object of the present invention is to provide an oiliness agent exhibiting very excellent emulsifying property with an oil, swelling property, thixotropy-imparting property, sedimentation-suppressing ability and viscosity-imparting property.

A further object of the present invention is to provide a water-in-oil type emulsion which can be effectively used as a base material for cosmetics, maintaining excellent dispersion stability and moisture; retaining property.

According to the present invention, there is provided an oiliness agent comprising a carboxylate of a composite metal hydroxide having a chemical composition represented by the following general formula (1),

$$M^2{}_a M^3{}_x(OH)_y(A)_z \cdot nH_2O \tag{1}$$

wherein,
$M^2$ indicates a divalent metal,
$M^3$ indicates a trivalent metal,
A indicates an anion of an aliphatic carboxylic acid,
a, x, y and z are numbers satisfying the following formulas:

$a > 0$, $3x + 2a - y - mz = 0$ (wherein m is a valency of anion A), $0.3 \leq a/x \leq 2.5$ $1.5 \leq y/(a+x) \leq 3.0$ $1.0 \leq (a+x)/z \leq 20.0$, and n is a number of not larger than 7.

In the oiliness agent of the present invention, it is desired that the carboxylate of the composite metal hydroxide contains at least zinc (Zn) as a divalent metal $M^{2\cdot}$ When divalent metals other than Zn are indicated by Q, it is desired that the carboxylate of the composite metal hydroxide has a chemical composition expressed by the following general formula (1a):

$$(Zn)_p(Q)_q M^3{}_x(OH)_y(A)_z \cdot nH_2O \tag{1a}$$

wherein,
$M^3$, A, b, x, y and z are as defined in the above general formula (1),
Q indicates a divalent metal other than Zn, and
p and q are the numbers satisfying the following formulas, $p + q = a$ (a is as defined in the general formula (1)), and $p/(p+q) \geq 0.1$.

It is most desired that the divalent metal Q other than zinc, is magnesium. It is further desired that the trivalent metal in the carboxylate of the composite metal hydroxide is aluminum (Al), and anion is a monovalent fatty acid having carbon atoms in a number of from 10 to 22 and, particularly, from 12 to 22.

The oiliness agent of the present invention can be effectively used as an emulsifier or a dispersant, as a thixotropy-imparting agent and as a viscosity-imparting agent. The water-in-oil emulsion (W/O emulsion) prepared by using the oiliness agent as an emulsifier, exhibits excellent dispersion stability and moisture retaining property without emitting odor or without the tendency of being colored, and is very useful as a base material for cosmetics.

DETAILED DESCRIPTION OF THE INVENTION

The present invention is based on a discovery that a carboxylate of a composite metal hydroxide represented by the above formula (1) exhibits very excellent properties as an oiliness agent and can be used as an emulsifier for stabilizing the dispersed state in, for example, a system in which water particles are dispersed in an oil.

The carboxylate of the composite metal hydroxide is substantially insoluble in water. As will be described later by way of Examples, however, it was learned that a water-in-oil type emulsion is stabilized if a powder of the carboxylate of the composite metal hydroxide is suspended in a fluidized paraffin, if water is added to a suspension thereof and if the mixture is stirred at a high speed.

That is, the formation of the water-in-oil type emulsion is confirmed as the mixture system becomes cloudy and as the viscosity of the mixture system rises. Here, the fact that the aqueous phase is in the form of independently dispersed particles can be confirmed relying upon that the moisture retaining ratio of the mixture system is strikingly increased compared to that of a simple mixture and that the electric conductivity of the mixture system is markedly decreased (see Examples appearing later). Further, the dispersion stability of the water-in-oil type emulsion can be confirmed by leaving the emulsion to stand for about a week and observing whether the emulsion has separated into phases due to gravity.

It is quite an astonishing fact that there is formed a stable water-in-oil type emulsion despite of the fact that the carboxylate of the composite metal hydroxide used in the present invention is substantially insoluble in water and is insoluble in an oil phase, either.

This fact was discovered as a phenomenon, and it is considered that the carboxylate of the composite metal hydroxide exhibits the emulsifying action as described below, though the reasons described below are in no way to restrict the present invention.

Figure 1:
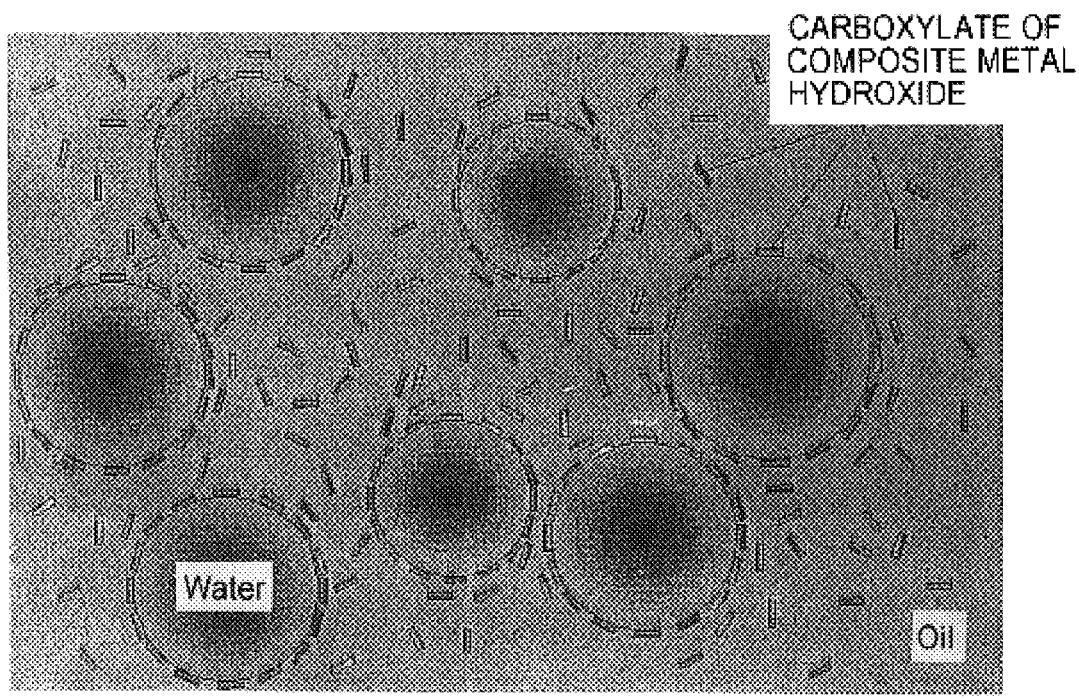
FIG. 1 is a model diagram of when a carboxylate of a composite metal hydroxide of the present invention is used as an emulsifier.

That is, the carboxylate of the composite metal hydroxide used in the present invention has a hydrophilic group which is a hydroxyl group and a nonpolar group (oleophilic group) based on a carboxylic acid. In the carboxylate of the composite metal hydroxide, therefore, it is presumed that the nonpolar groups (oleophilic groups) are arranged in the oil phase and the hydroxyl groups (hydrophilic groups) are arranged in the water phase to form a micelle structure contributing to stabilizing the water-in-oil emulsion. FIG. 1 is a model diagram of when the above-mentioned carboxylate of the composite metal hydroxide is used as the emulsifier.

The carboxylate of the composite metal hydroxide of the present invention has a feature in that it has a very large ability for taking in the oil phase. Namely, the oil phase is not atomized or dispersed but, instead, the oil phase is permitted to exist as a continuous phase and the water phase as a dispersion phase, enabling the dispersed particles to be atomized and stabilized. That is, the emulsifying action of the carboxylate of the composite metal hydroxide contributes to selectively forming the water-in-oil type emulsion.

Thus, the carboxylate of the composite metal hydroxide works as an excellent emulsifier for the water-in-oil emulsion. By using the trioctahedral clay mineral in combination, further, the content of the aqueous phase in the water-in-oil emulsion can be markedly increased without decreasing the dispersion stability or the moisture retaining ratio.

In a water-in-oil type emulsion using the carboxylate of the composite metal hydroxide alone as an emulsifier, the dispersion stability tends to slightly decrease as the amount of the aqueous phase exceeds 40% by weight. When the trioctahedral clay mineral is used in combination, on the other hand, the dispersion stability is maintained even when the amount of the aqueous phase is increased to 70% by weight. In the water-in-oil type emulsion formed by using the above-mentioned carboxylate of the composite metal hydroxide, it is desired that oil and water are existing at a weight ratio in a range of from 99.9:0.1 to 8:92 and, preferably, from 89:11 to 27:73. The diameter of the particles dispersed in water can be varied over a wide range of, generally, from 0.1 to 100 μm and, particularly, from 0.1 to 50 μm.

Figure 2:
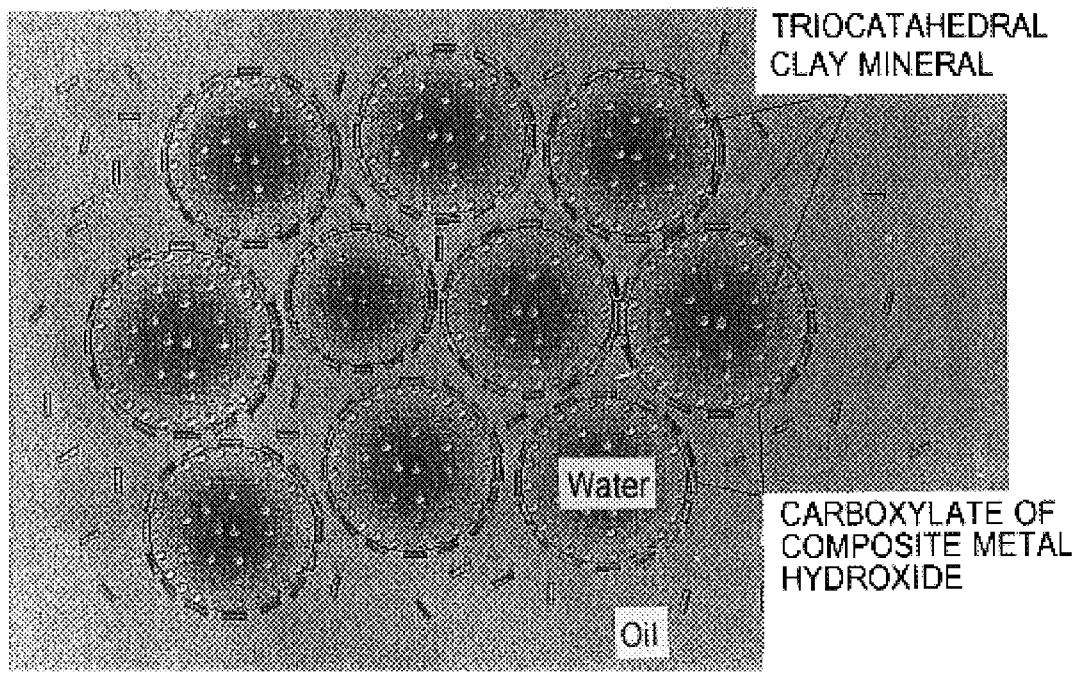
FIG. 2 is a model diagram of when a carboxylate of a composite metal hydroxide and a trioctahedral clay mineral are used in combination as an emulsifier.

FIG. 2 is a model diagram of a case when the carboxylate of the composite metal hydroxide and the trioctahedral clay mineral are used in combination as the emulsifier. When the trioctahedral clay mineral alone is used as the emulsifier, it is difficult to form the oil-in-water (O/W) type emulsion or to form the water-in-oil (W/O) type emulsion. It is therefore the greatest feature of the present invention to form the water-in-oil type emulsion by using the carboxylate of the composite metal hydroxide and the trioctahedral clay mineral in combination without using surfactant.

The trioctahedral clay mineral and, particularly, the stevensite clay mineral exhibits the following three properties in playing the role of an emulsifier: i.e., (1) It is hydrophilic as well as oleophilic;
(2) It's crystallite size is very fine and easily forms a gel upon absorbing water, and assumes a liquid state rich in fluidity if a shearing force is given to the gel; and
(3) It's cation-exchange capacity is smaller than that of the other clay minerals of the group of smectite, exhibiting a small activity in the aqueous solution.

The trioctahedral clay mineral in water swells upon absorbing water, whereby the fundamental layers that had been stacked disintegrate into pieces, crystals of clay minerals become continuous due to the relationship of positive and negative charges existing on the surfaces of the fundamental layers forming so-called card-house structures in many number thereby to form a gel having no fluidity. As a result, it is considered that water is fixed to maintain stability.

As will be understood from the above, the water-in-oil type emulsion formed by using the carboxylate of the composite metal hydroxide as an emulsifier is particularly effective as a base material for cosmetics, such as rouge and the like and as a cataplasm for medical treatment, that must possess water retaining property.

Further, the carboxylate of the composite metal hydroxide used in the present invention has a very large ability for taking in the oil phase compared to that of the trioctahedral clay mineral, and makes it possible to obtain a water-in-oil type emulsion using the trioctahedral clay mineral in combination by adding the carboxylate of the composite metal hydroxide to the oil phase, adding the trioctahedral clay mineral to the aqueous phase, and mixing them together with stirring.

As described above, the oiliness agent of the present invention comprising the carboxylate of the composite metal oxide is useful as an emulsifier or a dispersant and, particularly, as an emulsifier for forming the W/O emulsion.

Among the above-mentioned carboxylates of the composite metal oxide of the present invention, further, the one containing Zn as a divalent metal (carboxylate of the Zn-type composite metal hydroxide) has excellent properties such as swelling property by oil, thixotropy-imparting property, sedimentation-suppressing ability and viscosity-imparting property as compared to those without containing Zn (e.g., carboxylates of the Mg-type composite metal hydroxide), and is very useful as, for example, the thixotropy-imparting agent and the viscosity-imparting agent. Thixotropy is a property in that the viscosity decreases as the shearing force increases, and the viscosity increases as the shearing force decreases. Thixotropy is important for the oiliness agent. The oiliness agent of the present invention having excellent thixotropy offers a great advantage when it is used, for example, for an anti-sweating agent, cream, nail lacquer and cosmetics such as coloring material, cosmetic ink and soap.

[Carboxylates of Composite Metal Hydroxides]

A carboxylate of a composite metal hydroxide used in the present invention has a chemical composition represented by the following general formula (1), $$M^2{}_a M^3{}_x(OH)_y(A)_z \cdot nH_2O \qquad (1)$$

wherein,
M$^2$ indicates a divalent metal,
M$^3$ indicates a trivalent metal,
A indicates an anion of an aliphatic carboxylic acid,
a, x, y and z are numbers satisfying the following formulas:

a>0,

3x+2a−y−mz=0 (wherein m is a valency of anion A), 0.3≤a/x≤=2.5

1.5≤y/(a+x)≤3.0

1.0≤(a+x)/z≤20.0, and n is a number of not larger than 7.

In the carboxylate of the composite metal hydroxide used in the present invention, examples of the divalent metal M$^2$ include Mg, Zn, Be, Ca, Ba, Sr, Cd, Mn, Fe, Co, Ni, Cu, Pd, Sn, Pt and Pb. Here, however, it is desired that at least Zn is contained as the divalent metal M$^2$ As will be obvious from Examples appearing later, the carboxylate of the composite metal hydroxide containing Zn has a degree of whiteness of not smaller than 97% and is particularly useful as a base material for cosmetics.

It is, further, desired that the carboxylate of the Zn-containing composite metal hydroxide has a chemical composition represented by the following general formula (1a), $$(Zn)_p(Q)_q M^3{}_x(OH)_y(A)_z \cdot nH_2O \qquad (1a)$$

wherein,
M$^3$, A, b, x, y and z are as defined in the above general formula (1),
Q indicates a divalent metal other than Zn, and
p and q are the numbers satisfying the following formulas, p+q=a (a is as defined in the general formula (1)), and p/(p+q)≧0.1.

It is most desired that the divalent metal Q other than zinc, is magnesium.

As the trivalent metal M$^3$ of the carboxylate of the composite metal hydroxide, there can be exemplified Al, Sc, Ti, V, Cr, Mn, Fe, Co. Ni, Ga, Y, Ru, Rh, In, Sb, La, Ce, Nd, Pm, Sm, Eu, Gd, Tb, Dy, Ho, Er, Tm, Yb, Lu, Os, Ir, Au, Bi, Ac and Th. Among them, Al is preferred.

It is desired that the anion of the carboxylate of the composite metal hydroxide is a monovalent fatty acid having carbon atoms in a number of from 10 to 22 and, particularly, from 12 to 22. Examples include saturated fatty acids such as lauric acid, tridecylic acid, myristic acid, pentadecylic acid, palmitic acid, heptadecylic acid, stearic acid, nonadecanoic acid, arachic acid and behenic acid, as well as unsaturated fatty acids such as oleic acid, linolic acid, linoleic acid, and arachidonic acid. Among them, stearic acid is preferred.

The carboxylate of the composite metal hydroxide having the above chemical composition has a fundamental layer in which M$^2$ in the octahedral layer of M$^2$(OH)$_6$ is replaced by M$^3$ of the same type, the anions being incorporated among the fundamental layers in a form being balanced with excess of cations (M$^3$) introduced by substitution. The fundamental structures are stacked in many number to form a layered crystalline structure.

Figure 3:
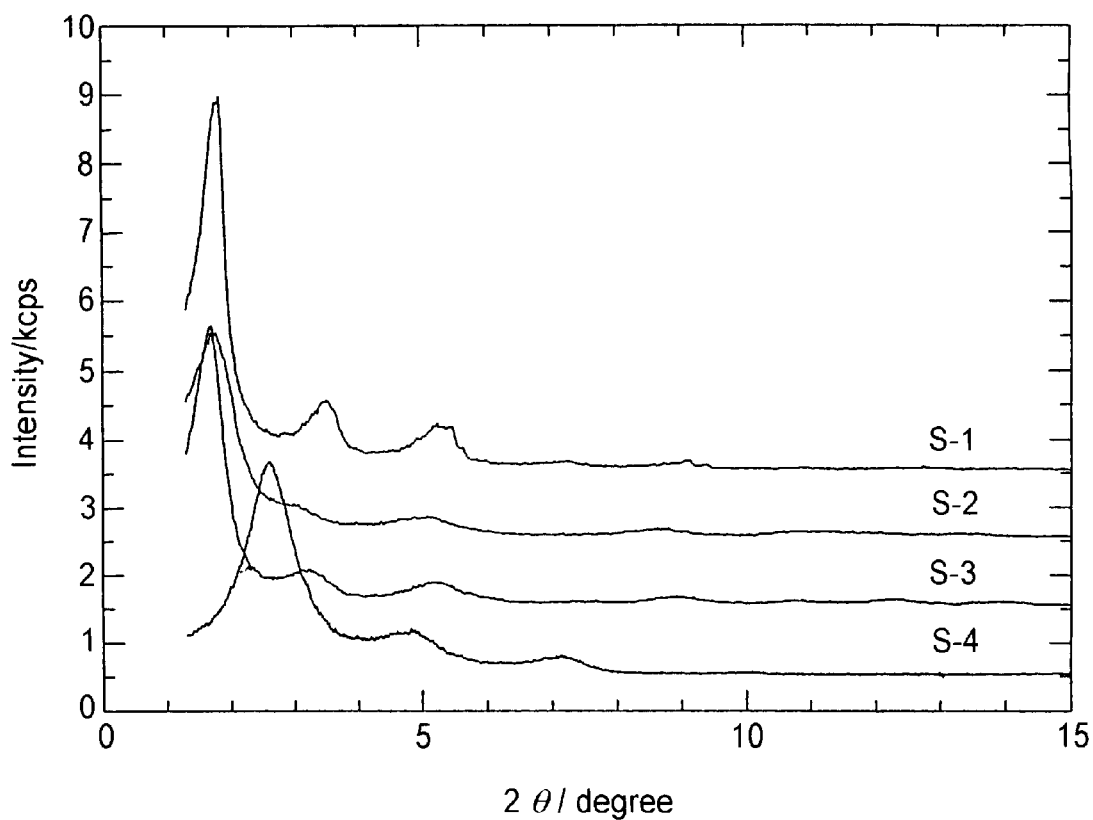
FIG. 3 is a diagram of X-ray diffraction images of the carboxylate of the composite metal hydroxide and of an organic modified bentonite.

In the present invention, it is desired that the carboxylate of the composite metal hydroxide has a diffraction peak at 2θ=1 to 2.5° in the X-ray diffraction (Cu-kα). FIG. 3 shows the X-ray diffraction images of the carboxylate of the composite metal hydroxide and of an organic modified bentonite. The carboxylate of the composite metal hydroxide has a diffraction peak at 2θ=about 1.8° (samples S-1 to S-3 described later) while the organic modified bentonite has a diffraction peak at 2θ=about 2.6° (sample S-4 described later), from which it will be learned that the carboxylate of the composite metal hydroxide is different from the organic bentonite.

The organic bentonite is generally the one in which a quaternary ammonium salt is intercalated among the bentonite layers involving problems in regard to safety and odor. The carboxylate of the composite metal hydroxide of the present invention does no contain such a quaternary ammonium salt, and is free from the problems of safety (stimulation to the skin) and odor and is, hence, useful as a base material for cosmetics.

The carboxylate of the composite metal hydroxide can be directly synthesized but is obtained by, first, synthesizing a composite metal hydroxide and, then, ionically exchanging the anions in the composite metal hydroxide with an aliphatic carboxylic acid.

As the composite metal hydroxide used for obtaining a carboxylate of the composite metal hydroxide by the ion-exchange method, there can be used those of the following two kinds (first and second composite metal hydroxides).

(First Composite Metal Hydroxide)

This composite metal hydroxide has a chemical composition represented by the following general formula (2), $$M^2_a M^3_x (OH)_y (B)_z \cdot nH_2O \qquad (2)$$

wherein,
$M^2$ indicates a divalent metal,
$M^3$ indicates a trivalent metal,
B indicates an inorganic anion component such as sulfuric acid, and
a, x, y and z are numbers satisfying the conditions same as those of the general formula (1).

The above composite metal hydroxide is obtained by reacting, for example, a water-soluble salt of a trivalent metal with an oxide, a hydroxide or a water-soluble salt of a divalent metal under the conditions of a pH of from 3.5 to 10.0 and a temperature of not lower than 50° C.

Upon exchanging the ions of the thus obtained first composite metal hydroxide in the presence of an alkali metal salt of an aliphatic carboxylic acid, there is obtained a carboxylate of a composite metal hydroxide that can be used in the present invention.

(Second Composite Metal Hydroxide)

The second composite metal hydroxide is a hydrotalcite which is a synthetic mineral pertaining to an magnesium aluminum carbonate hydroxide. The magnesium aluminum carbonate hydroxide has a general chemical composition represented by the following formula (3), $$M^2_x M^3_y (OH)_{2x+3y-2z} (B^{2-})_z \cdot aH_2O \qquad (3)$$

wherein,
$M^2$ indicates a divalent metal ion such as Mg,
$M^3$ indicates a trivalent metal ion such as Al,
$B^{2-}$ indicates a divalent anion such as $CO_3$,
x, y and z are positive numbers satisfying the following formula:

$8 \geq x/y \geq 1/4$ and $z/x+y > 1/20$, and a is a number satisfying $0.25 \leq a/x+y \leq 1.0$.

The hydrotalcite is a mineral which is one of the above-mentioned magnesium aluminum carbonate hydroxides, and is represented by the following formula (4), $$Mg_6Al_2(OH)_{16}(CO_3) \cdot 4H_2O \qquad (4)$$

The above mineral and homologues can be synthesized by the methods disclosed in Japanese Examined Patent Publications Nos. 32198/1972, 29477/1973 and 29478/1973 filed by Kyowa Kagaku Kogyo Co.

The hydrotalcite containing zinc (hydrotalcite modified with zinc) generally has a chemical composition represented by the following formula (5), $$[Mg_y Zn_z]_{1-x} Al_x (OH)_2 B_{x/n} \cdot mH_2O \qquad (5)$$

wherein,
B is a monovalent or divalent anion,
y, z and x are numbers satisfying the following conditions:

$0.15 < z/(y+z) < 0.4$, and $0 < x < 0.6$, n is a valency of anion B, and
m is a positive number.

That is, among the above hydrotalcites, there is selected the one capable of forming a carboxylate of a composite metal hydroxide having a composition as represented by the general formula (1) and is put to the anion exchange.

Here, in general, it is difficult to exchange anions having a large molecular weight such as of aliphatic carboxylic acid with anions of the hydrotalcite. It is therefore desired to once fire the hydrotalcite at 500 to 700° C. to split off the anions in the hydrotalcite and, then, exchange the ions. It is further possible to once exchange the ions with anions that can be easily exchanged, e.g., with the ions of the sulfuric acid-type hydrotalcite and, then, exchange the ions with the ions of the aliphatic carboxylic acid.

The oiliness agent of the present invention comprising the carboxylate of the composite metal hydroxide can be added to such cosmetics as lotions, creams, shampoos, rinse, hair tonics, liquid soaps and the like in order to improve emulsion stability, to adjust viscous properties and to improve dispersion of pigment.

The oiliness agent of the invention can be further added to medicines, agricultural chemicals and products not pertaining to medicines in order to adjust the fluidity, to stabilize the viscosity, to stabilize the base for forming gel and to stabilize the dispersion of various components.

The oiliness agent of the present invention can be further used for cleaners, polishing compounds and cleansers for the domestic products such as metals, cars, glasses, tiles, floors and ceramics to accomplish the same object as the one described above.

The oiliness agent of the invention can be further used as a stabilizer, a viscosity-imparting agent, a thixotropy-imparting agent or as a dripping-preventing agent even for the industrial products such as various emulsion paints, latexes and adhesives.

Even in the fields of agricultural products and foods, the oiliness agent of the invention can be used as various culture grounds in the form of a gel in order to purify the fermented products, or as a viscosity-imparting agent or as an emulsion stabilizer.

[Trioctahedral clay minerals]

As described already, the carboxylate of the composite metal hydroxide can be very excellently used as an emulsifier for forming the W/O emulsion. By using the carboxylate of the composite metal oxide in combination with the trioctahedral clay mineral, it is allowed to form a W/O emulsion which is more stabilized.

As the trioctahedral clay minerals there can be exemplified the following compounds (in the following formulas, X indicates K, Na, ½ Ca or ½ Mg).

1. Saponite of which the ideal composition is, $$X_{0.33}(Mg_3)(Si_{3.67}Al_{0.33})O_{10}(OH)_2 \cdot nH_2O$$

2. Iron saponite of which the ideal composition is, $$X_{0.33}(Mg, Fe)_3(Si_{3.67}Al_{0.33})O_{10}(OH)_2 \cdot nH_2O$$

3. Hectorite of which the ideal composition is, $$X_{0.33}(Mg_{2.67}Li_{0.33})Si_4O_{10}(OH)_2 \cdot nH_2O$$

4. Sauconite of which the ideal composition is, $$X_{0.33}(Mg, Zn)_3(Si_{3.67}Al_{0.33})O_{10}(OH)_2 \cdot nH_2O$$

5. Stevensite of which the ideal composition is, $$X_{0.33/2}(Mg_{2.97}Si_4O_{10}(OH)_2 \cdot nH_2O$$

Among the above trioctahedral clay minerals, the most preferred example is the stevensite.

Figure 4:
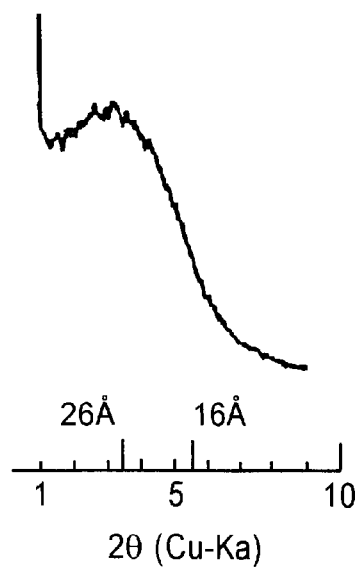
FIG. 4 is a diagram of an X-ray diffraction image of a synthetic stevensite which is a trioctahedral clay mineral in a state of being treated with an ethylene glycol.

It is desired that the trioctahedral clay mineral is the one in which the metal component is a sodium magnesium phillosilicate comprising substantially magnesium, sodium and silicon only, and having an X-ray diffraction peak in a spacing of 16 to 26 angstroms in a state of being treated with an ethylene glycol. FIG. 4 illustrates the X-ray diffraction image of when measured in the state of being treated with the ethylene glycol.

In the present invention, a preferred stevensite has a chemical composition expressed by the following formula (6), $$Mg_xNa_ySi_4O_{10}(OH)_2 \cdot Na_z \qquad (6)$$

wherein,
x is a number of not smaller than 2, and
y is a number of from 0 to 0.1
under a condition where x+y<3, and
z is a number of up to 1.0 but is not smaller than 0.

The above stevensite can be synthesized by, for example, subjecting an aqueous composition containing a basic magnesium carbonate and a silica-sodium component (e.g., (i) sodium silicate, (ii) sodium silicate and amorphous silica, or (iii) amorphous silica and sodium hydroxide) to the hydrothermal treatment.

The hydrothermal treatment can be conducted by feeding the above aqueous composition into an autoclave. The hydrothermal treatment is conducted under the conditions of a temperature of, for example, from 100 to 300° C. and, particularly, from 150 to 200° C. under a pressure of from 0 to 100 kg/cm² (gauge) and, particularly, from 6 to 40 kg/cm² (gauge). The reaction time is generally of the order of from 0.5 to 20 hours. The stevensite formed by the reaction is obtained by separating it from the mother liquid by solid-liquid separation, washing it with water and drying it.

The synthetic stevensite obtained by the above method is a white powder having the Hunter's degree of whiteness of, usually, not smaller than 80% and, particularly, not smaller than 90%, and having a cation-exchange capacity of, usually, from 0.20 to 1.58 milliequivalent (meq)/g and, particularly, from 0.2 to 1.0 meq/g. The synthetic stevensite further has a relatively large specific surface area, i.e., a BET specific surface area which is, generally, from 200 to 500 m²/g and, particularly, from 350 to 450 m²/g.

According to the present invention, the W/o emulsion having an oil phase as a continuous phase and water as a dispersion phase is formed by using the above-mentioned carboxylate of the composite metal hydroxide as an emulsifier and, as required, by using the above-mentioned trioctahedral clay mineral in combination. In the W/O emulsion, the oil component in the oil phase includes all materials which are usually expressed by a word "oil" in foods, cosmetics, medicines, etc., and refers widely to polar oils through up to nonpolar oils. They include even those oil components which remain solid at normal temperature, which maintain in a liquid state being heated prior to effecting the emulsifying operation or during the emulsifying operation or by any other method, as well as composite oil components in which various compounds are dissolved, partly substituted or dispersed in the oil components. Therefore, a variety of oil components can be used depending upon the use of the W/o emulsion.

Concrete examples of these oil components include, though not limited thereto only, animal and plant oils such as fluidized paraffin, squalane, olive oil, evening primrose oil, rice bran oil, candelilla wax, carnauba wax, beef tallow, isoparaffin and branched chain light paraffin; ester oils such as hydrocarbon oil, isopropyl myristate, cetyl isooctanoate, glyceryl trioctanoate, pentaerythritol-tetra-2-ethyl hexanate; silicone oils such as methylphenyl silicon, dimethyl silicon, and decamethyl pentacyloxane; alcohols such as 2-octyldodecanol, 2-decyltetradecanol, stearyl alcohol, oleyl alcohol and cetyl alcohol; fatty acids such as behenic acid, oleic acid, stearic acid, isostearic acid and hydroxystearic acid; and vaseline, hydrous lanolin, microcrystalline wax and bees wax.

The aqueous solution in the W/O emulsion needs not be limited to pure water but may be a solution of water in which are dissolved various compounds such as hydrocarbons, amino acid, proteins, water-soluble compounds, pigment, perfume, drug, crude drug, surfactant, viscosity-imparting agent, antiseptic, metallic ion-blocking agent and ultraviolet-absorbing agent, or a dispersion of water in which the above compounds are dispersed.

The emulsifying operation for forming the W/o emulsion may just be the widely employed physical or chemical emulsifying technology. A representative physical method may be the one that utilizes the mechanical force for producing a strong shearing force, such as the one using a homogenizer, a colloid mill, a votator or a jet flow mixer. As the chemical method, further, there has been developed a new emulsifying technology accompanying the elucidation of physicochemical phenomena such as micellar dissolution, inverse micelle and liquid crystals as exemplified by an inverse emulsifying method, an HLB-temperature emulsifying method, a surfactant phase emulsifying method and a gelled emulsifying method.

EXAMPLES

The invention will now be described by way of the following Examples to which only, however, the invention is in no way limited.

The testings were conducted according to the methods described below.
(1) X-Ray Diffraction.

Measured with Cu-Kα by using a RAD-IB system of Rigaku Denki Co.

| | |
|---|---|
| Target | Cu |
| Filter | Ni |
| Detector | SC |
| Voltage | 40 KV |
| Current | 20 mA |
| Count full-scale | 8000 c/s |
| Scanning speed | 1°/min |
| Step sampling | 0.017° |
| Slit | DS ½° RS 0.05 mm |
| | SS ½° |
| Illuminating angle | 6° |
| Measuring range of diffraction angles | 1° to 15° (2θ) |

(2) X-Ray Diffraction by the Treatment with an Ethylene Glycol.

5 Milliliters of an aqueous solution containing 10% of an ethylene glycol was added by using a whole pipette to 1.0 g of a sample dried at 110° C. for 2 hours, mixed well by using a stirrer rod, and the mixture was dried at 60° C. for 12 hours. The dried product was crushed in an agate mortar and was measured under the following conditions.

| | |
|---|---|
| Target | Cu |
| Filter | Ni |
| Detector | SC |
| Voltage | 40 KV |
| Current | 20 mA |
| Count full-scale | 2000 c/s |
| Scanning speed | 1°/min |
| Step sampling | 0.033° |
| Slit | DS 1/6° RS 0.3 mm |
| | SS 1/6° |
| Illuminating angle | 6° |
| Measuring range of diffraction angles | 1° to 9° (2θ) |

The spacing (d) was calculated from a diffraction angle (2θ) found from an intermediate point in the half-value width in compliance with the following formula (7), $$d=(\lambda/2)\sin^{-1}(\theta) \quad (7)$$

wherein λ is a wavelength, 1.542 Å, of X-ray.

(3) Chemical Composition.

The chemical analysis was conducted by the wet-type analysis, atomic absorptive analysis and ion chromatography.

(4) Average Particle Diameter.

An average particle diameter was measured by using a particle size analyzer, Model LS230, manufactured by Coulter Co.

(5) Apparent Specific Eight.

Measured in compliance with JIS R 6220 (iron cylinder method).

(6) Degree of Whiteness.

Measured in compliance with JIS P 8123.

(Evaluation of W/O Emulsion)

(7) Stability of Emulsion, Tint, Odor.

The emulsion was left to stand in the constant-temperature vessels maintained at room temperature and at 50° C. for one week, to observe whether it has separated into phases due to gravity, thereby to evaluate the stability as follows:

○: Stable,

×: Separation into phases is recognized on the surface of the emulsion.

The tint of the emulsion was observed by naked eyes, and the odor was judged by smelling the odor.

(8) Electric Conductivity.

Measured by using an electric conductivity meter (DS-14) manufactured by Horiba Seisakusho Co.

The electric conductivity is an index indicating the emulsified stability of the W/O emulsion. The smaller this value (unit in $\mu$S/cm), the higher the emulsified stability of the W/O emulsion.

(9) Moisture Retaining Ratio.

The moisture retaining ratio was found by putting the sample into a desiccator in which the relative humidity has been adjusted to 20% (25° C.) and by measuring a reduction in the weight of the emulsion in accordance with JIS Z 0701. A reduction in the weight of the emulsion was also measured in a constant-temperature vessel maintained at 50° C.

(10) Testing the Swelling Property.

50 Milliliters of a fluidized paraffin and 1 g of a sample were added into a 100-ml messcylinder, sealed and were shaked by using a shaking machine for three minutes. After left to stand still for 72 hours, the sedimented volume was measured. The sedimented volume is an index that represents the dispersion of when a small shearing force is acted. The larger the sedimented volume, the more the sample is swollen in the fluidized paraffin and is easily dispersed.

(11) Testing the Dispersion Stability (Suppressing the Sedimentation).

15 Grams of an active terra abla (80% of which having a particle size of 5 to 55 $\mu$m) insoluble in fluidized paraffin and 2 g of the sample were added to 100 g of the fluidized paraffin, and the mixture was treated by using a homomixer at 5000 rpm for 5 minutes. After left to stand still for 5 minutes, 100 ml of the mixture dispersion was transferred into a 100-ml messcylinder to measure the sedimented volume after 24 hours have passed.

The larger the sedimented volume, the better the dispersion stability of the suspension product in the fluidized paraffin, excellently suppressing the sedimentation.

(12) Testing the Thixotropic Property.

30 Grams of a sample was added to 170 g of the fluidized paraffin, and the mixture was heated at 90° C. and was stirred by using the homomixer at 2000 rpm for 5 minutes. After left to stand still, the viscosity (20° C.) of the suspension was measured by using a viscometer, DVL-BII, manufactured by Tokyo Keiki Co. while changing the rotational speed of the rotor from 3 rpm to 60 rpm (up) and from 60 rpm to 3 rpm (down). The thixotropic property is expressed by the following formula, $$T=\eta_3/\eta_{60}$$

wherein, $\eta_3$ is a viscosity of when the rotor rotational speed is 3 rpm, and $\eta_{60}$ is a viscosity of when the rotor rotational speed is 60 rpm.

(Sample Preparation 1)

Into a 1-liter beaker containing 371 g of ion-exchanged water, there were added:

47.0 g of ammonium chloride (purity, 98.5%), 70.7 g of zinc oxide (ZnO=99.6%), and 52.9 g of magnesium hydroxide (MgO=65.9%), and the mixture was mixed well. To the thus obtained slurry was gradually poured 400 g of an alumina sulfate ($Al_2O_3$= 7.78%, $SO_3$=18.4%) at room temperature with stirring, and the mixture was heated up to 95° C. and was reacted for 20 hours. After the reaction, the reaction product was filtered and was washed with hot water of an amount twice as much as the reaction solution to obtain a filtered cake.

Then, 50 g of the filtered cake (calculated as dry cake at 110° C.) was measured and was introduced into a 2-liter beaker, ion-exchanged water was added thereto to disperse the cake again, followed by the addition of ion-exchanged water to obtain a 10% slurry thereof which was, then, heated at 70° C. to obtain a hydrate thereof.

Ion-exchanged water was poured into another beaker, heated at 85° C., sodium hydroxide (in an amount equivalent to stearic acid to be added next time) was added thereto and, then, 61.3 g of stearic acid (2.5 mol times as much as $SO_3$ in the hydrate) was thrown therein. While maintaining the temperature at 85° C., the concentration of the sodium stearate solution was adjusted with ion-exchanged water to be 10% by weight, which was, then, gradually poured to the above hydrate to conduct the anion-exchange reaction at 70° C. for one hour.

Then, the reaction product was filtered, washed with hot water of an amount twice as much as the reaction solution, and was dried a whole day at 110° C. followed by pulverization to obtain a white powder thereof.

The analysis of the obtained white powder indicated that the synthesized product possessed the following molar composition ratio,

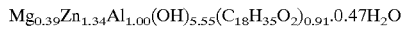

$Mg_{0.39}Zn_{1.34}Al_{1.00}(OH)_{5.55}(C_{18}H_{35}O_2)_{0.91} \cdot 0.47H_2O$

This sample was labeled as S-1. FIG. 3 shows the X-ray diffraction image of the sample S-1, and Table 1 shows properties of the powder thereof.

(Sample Preparation 2)

Into a 2-liter beaker containing 293 g of ion-exchanged water, there were added:

156 g of magnesium chloride hexahydrate (purity, 98%), and 219 g of an alumina sulfate ($Al_2O_3$=7.78%, $SO_3$=18.4%), and the mixture was mixed well. The obtained solution was gradually poured with stirring at room temperature into an aqueous solution of sodium hydroxide comprising 90 g of sodium hydroxide (purity, 96%) and 632 g of ion-exchanged water. After the addition, the hydrothermal synthesis was conducted in a 1.5-liter autoclave at 170° C. for 6 hours. After the reaction, the reaction product was filtered and was washed with hot water of an amount twice as much as the reaction solution to obtain a filtered cake thereof.

Then, 50 g of the filtered cake (calculated as dry cake at 110° C.) was measured and was introduced into a 2-liter beaker, ion-exchanged water was added thereto to disperse the cake again, followed by the addition of ion-exchanged water to obtain a 10% slurry thereof which was, then, heated at 70° C. to obtain a hydrate thereof.

Ion-exchanged water was poured into another beaker, heated at 85° C., sodium hydroxide (in an amount equivalent to stearic acid to be added next time) was added thereto and, then, 60.4 g of stearic acid (2.5 mol times as much as $SO_3$ in the hydrate) was thrown therein. While maintaining the temperature at 85° C., the concentration of the sodium stearate solution was adjusted with ion-exchanged water to be 10% by weight, which was, then, gradually poured to the above hydrate to conduct the anion-exchange reaction at 70° C. for one hour.

Then, the reaction product was filtered, washed with hot water of an amount twice as much as the reaction solution, and was dried a whole day at 110° C. followed by pulverization to obtain a pale yellow powder thereof.

The analysis of the obtained pale yellow powder indicated that the synthesized product possessed the following molar composition ratio,

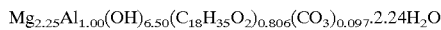

$Mg_{2.25}Al_{1.00}(OH)_{6.50}(C_{18}H_{35}O_2)_{0.806}(CO_3)_{0.097} \cdot 2.24H_2O$ This sample was labeled as S-2. FIG. 3 shows the X-ray diffraction image of the sample S-2, and Table 1 shows properties of the powder thereof.

(Sample Preparation 3)

Into a 2-liter beaker containing 243 g of ion-exchanged water, there were added:

136 g of magnesium chloride hexahydrate (purity, 98%), 13.0 g of zinc chloride (purity, 98%), and 246 g of an alumina sulfate ($Al_2O_3$=7.78%, $SO_3$=18.4%), and the mixture was mixed well. The obtained solution was gradually poured with stirring at room temperature into an aqueous solution of sodium hydroxide comprising 94 g of sodium hydroxide (purity, 96%) and 656 g of ion-exchanged water. After the addition, the hydrothermal synthesis was conducted in a 1.5-liter autoclave at 150° C. for 10 hours. After the reaction, the reaction product was filtered and was washed with hot water of an amount twice as much as the reaction solution to obtain a filtered cake thereof.

Then, 50 g of the filtered cake (calculated as dry cake at 110° C.) was measured and was introduced into a 2-liter beaker, ion-exchanged water was added thereto to disperse the cake again, followed by the addition of ion-exchanged water to obtain a 7.5% slurry thereof which was, then, heated at 70° C. to obtain a hydrate thereof.

Ion-exchanged water was poured into another beaker, heated at 85° C., sodium hydroxide (in an amount equivalent to stearic acid to be added next time) was added thereto and, then, 60.4 g of stearic acid (2.5 mol times as much as $SO_3$ in the hydrate) was thrown therein. While maintaining the temperature at 85° C., the concentration of the sodium stearate solution was adjusted with ion-exchanged water to be 10% by weight, which was, then, gradually poured to the above hydrate to conduct the anion-exchange reaction at 70° C. for one hour.

Then, the reaction product was filtered, washed with hot water of an amount twice as much as the reaction solution, and was dried a whole day at 110° C. followed by pulverization to obtain a white powder thereof.

The analysis of the obtained white powder indicated that the synthesized product possessed the following molar composition ratio,

$Zn_{0.25}Mg_{1.75}Al_{1.00}(OH)_{6.00}(C_{18}H_{35}O_2)_{0.808}(CO_3)_{0.096} \cdot 2.24H_2O$ This sample was labeled as S-3. FIG. 3 shows the X-ray diffraction image of the sample S-3, and Table 1 shows properties of the powder thereof.

(Sample Preparation 4)

An organic bentonite was prepared by the cation-exchange reaction of an Na-type montmorillonite (Kunipia F, manufactured by Kunimine Kogyo Co.) and a quaternary ammonium salt (distearyldimethylammonium chloride, Coatamine D86P, manufactured by Kao Co.) by the following method.

200 Grams of the Na-type montmorillonite (calculated as dry product at 110° C.) was measured and was introduced into a 10-liter beaker, ion-exchanged water was added thereto to disperse the product again, followed by the addition of ion-exchanged water to obtain a 4% slurry thereof which was, then, heated at 80° C. to obtain a hydrate thereof.

Ion-exchanged water was poured into another beaker, heated at 80° C., and the quaternary ammonium salt (Coatamine D86P) was added thereto in a manner that the cation-exchange ability was 1.25 times as much as that of the hydrate. While maintaining the temperature at 80° C., the concentration of the Coatamine D86P was adjusted with ion-exchanged water to be 6% by weight, which was, then, gradually poured to the above hydrate.

After the cation-exchange reaction was conducted at 80° C. for one hour, the reaction product was filtered, washed with hot water of an amount twice as much as the reaction solution, and was dried a whole day at 110° C. followed by pulverization to obtain a brown organic bentonite powder.

This sample was labeled as S-4. FIG. 3 shows the X-ray diffraction image of the sample S-4, and Table 1 shows properties of the powder thereof.

(Sample Preparation 5)

Into 400 ml of water were introduced, 25.6 g of a commercially available basic magnesium carbonate (TT, manufactured by Tokuyama Co.), and 108 g of sodium silicate No. 3 (silica component, 24.0 g), and the mixture was mixed together in a household mixer for 3 minutes.

The volume of the solution was increased into 600 ml with ion-exchanged water, and the solution was poured into an autoclave having a content of one liter. A carbonic acid gas was blown therein with stirring. The blow was discontinued when the solution lost the fluidity. The hydrothermal synthesis was conducted at 180° C. for 3 hours, and the reaction product was left to cool. The reaction product was then filtered, washed with water and was dried to obtain 38.2 g of a synthetic stevensite.

This sample was labeled as S-5. FIG. 4 shows the X-ray diffraction image of the sample S-5 treated with an ethylene glycol.

TABLE 1

| | Sample | | | |
|---|---|---|---|---|
| Item | S-1 | S-2 | S-3 | S-4 |
| Particle size ($\mu$m) | 1.042 | 1.409 | 0.589 | 2.759 |
| Apparent specific gravity (g/mL) | 0.262 | 0.252 | 0.248 | 0.215 |
| Whiteness | 98.8 | 95.0 | 97.6 | 88.4 |

Example 1

Into 300-ml beaker were added 30 g of an emulsifier (sample S-1) and 170 g of a fluidized paraffin, and the mixture was heated at 90° C. and was stirred by using a T.K. homomixer (Tokushu Kika Kogyo Co.) at 2000 rpm for 5 minutes. After stirring, the mixture was deaerated and cooled for 2 hours in vacuum, and was used as a fluidized paraffin suspension (labeled as LPS-1).

The obtained fluidized paraffin suspension (LPS-1) was heated at 70° C. with stirring by using the T.K. homomixer.

Then, ion-exchanged water was added thereto little by little such that LPS-1:ion-exchanged water=90:10 (weight ratio). After stirred at 70° C. at 10,000 rpm for 10 minutes, the mixture was deaerated and cooled for 2 hours in vacuum to obtain a W/O type emulsion (content of the sample S-1, 13.5% by weight).

Table 2 shows the evaluated results of the obtained emulsion.

Example 2

A W/O type emulsion (content of the sample S-1, 10.5% by weight) was obtained in the same manner as in Example 1 but adding ion-exchanged water in such an amount that LPS-1:ion-exchanged water=70:30 (weight ratio).

Figure 5:
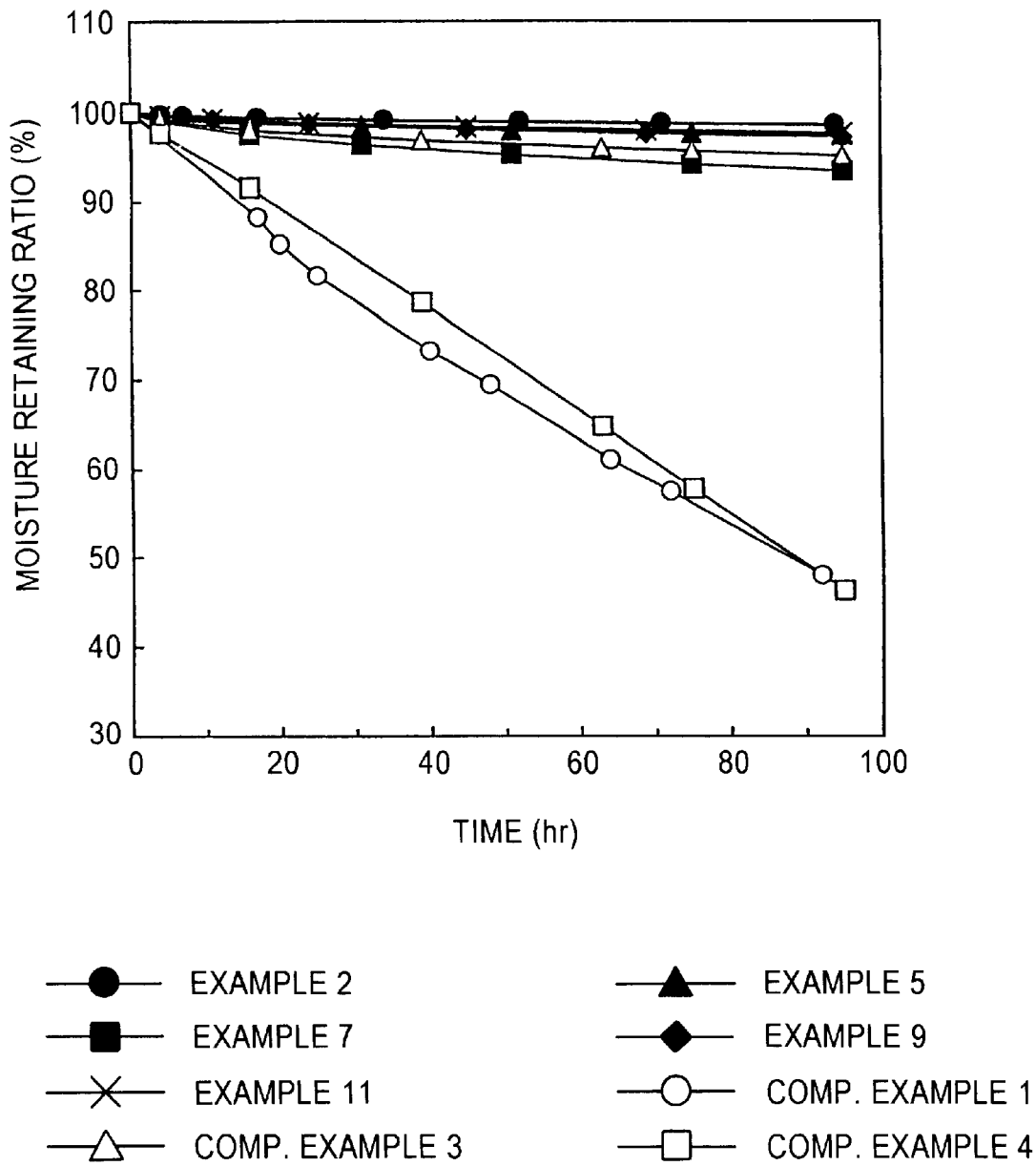
FIG. 5 is a diagram illustrating the moisture retaining ratios of the emulsions as found from the reduction of weight by introducing the samples into a desiccator in which the moisture is adjusted to be a relative humidity of 20% (25° C.) in compliance with JIS Z 0701.
Figure 6:
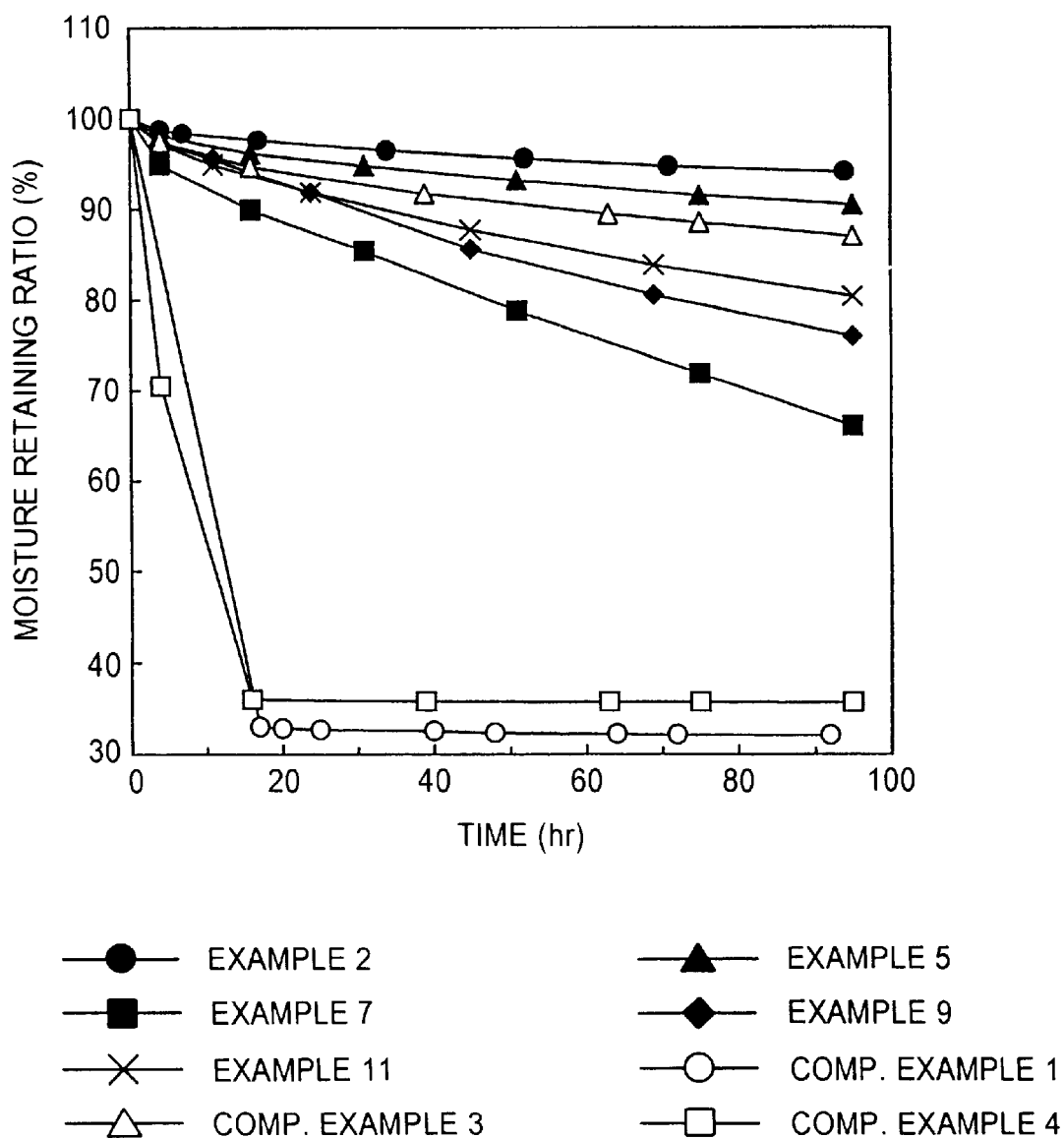
FIG. 6 is a diagram illustrating the moisture retaining ratios of the emulsions as found from the reduction of weight in a constant-temperature vessel maintained at 50° C.

Table 2 shows the evaluated results of the obtained emulsion. The moisture retaining ratio was as shown in FIG. 5 (relative humidity of 20%) and in FIG. 6 (50° C. constant-temperature vessel).

Example 3

6 Grams of an emulsifier (sample S-5) and 194 g of ion-exchanged water were introduced into a 300-ml beaker and were stirred for 2 hours by using a stirrer. The solution was labeled as S-5.

Next, the suspension (LPS-1) prepared in Example 1 was heated at 70° C. while being stirred by using the T.K. homomixer, and the solution S-5 was added thereto little by little such that LPS-1:solution S-5=70:30 (weight ratio). After stirred at 10,000 rpm for 10 minutes, the mixture was deaerated and cooled for 2 hours in vacuum to obtain a W/O type emulsion (content of the sum of the sample S-1 and the sample S-5, 11.4% by weight).

Table 2 shows the evaluated results of the obtained emulsion.

Example 4

A W/O type emulsion (content of the sum of the sample S-1 and the sample S-5, 10.2% by weight) was obtained in the same manner as in Example 3 but by mixing the suspension LPS-1 and the solution S-5 at such a ratio that LPS-1:solution S-5=60:40 (weight ratio).

Table 2 shows the evaluated results of the obtained emulsion.

Example 5

A W/O type emulsion (content of the sum of the sample S-1 and the sample S-5, 9.0% by weight) was obtained in the same manner as in Example 3 but by mixing the suspension LPS-1 and the solution S-5 at such a ratio that LPS-1:solution S-5=50:50 (weight ratio).

Table 2 shows the evaluated results of the obtained emulsion. The moisture retaining ratio was as shown in FIG. 5 (relative humidity of 20%) and in FIG. 6 (50° C. constant-temperature vessel).

Example 6

A W/O type emulsion (content of the sum of the sample S-1 and the sample S-5, 7.8% by weight) was obtained in the same manner as in Example 3 but by mixing the suspension LPS-1 and the solution S-5 at such a ratio that LPS-1:solution S-5=40:60 (weight ratio).

Table 2 shows the evaluated results of the obtained emulsion.

Example 7

A W/O type emulsion (content of the sum of the sample S-1 and the sample S-5, 6.6% by weight) was obtained in the same manner as in Example 3 but by mixing the suspension LPS-1 and the solution S-5 at such a ratio that LPS-1:solution S-5=30:70 (weight ratio).

Table 2 shows the evaluated results of the obtained emulsion. The moisture retaining ratio was as shown in FIG. 5 (relative humidity of 20%) and in FIG. 6 (50° C. constant-temperature vessel).

Example 8

A W/O type emulsion (content of the sum of the sample S-1 and the sample S-5, 11.4% by weight) was obtained in the same manner as in Example 3 but by preparing the suspension (LPS-2) by using the emulsifier (S-2) instead of the emulsifier (S-1).

Table 2 shows the evaluated results of the obtained emulsion.

Example 9

A W/O type emulsion (content of the sum of the sample S-2 and the sample S-5, 9.0% by weight) was obtained in the same manner as in Example 8 but by mixing the suspension LPS-2 and the solution S-5 at such a ratio that LPS-2:solution S-5=50:50 (weight ratio).

Table 2 shows the evaluated results of the obtained emulsion. The moisture retaining ratio was as shown in FIG. 5 (relative humidity of 20%) and in FIG. 6 (50° C. constant-temperature vessel).

Example 10

A W/O type emulsion (content of the sum of the sample S-3 and the sample S-5, 11.4% by weight) was obtained in the same manner as in Example 8 but by preparing the suspension (LPS-3) by using the emulsifier (S-3) instead of the emulsifier (S-2).

Table 2 shows the evaluated results of the obtained emulsion.

Example 11

A W/O type emulsion (content of the sum of the sample S-3 and the sample S-5, 9.0% by weight) was obtained in the same manner as in Example 10 but by mixing the suspension LPS-3 and the solution S-5 at such a ratio that LPS-3:solution S-5=50:50 (weight ratio).

Table 2 shows the evaluated results of the obtained emulsion. The moisture retaining ratio was as shown in FIG. 5 (relative humidity of 20%) and in FIG. 6 (50° C. constant-temperature vessel).

Comparative Example 1

An emulsion was prepared in the same manner as in Example 3 but without adding the emulsifier (S-1) to the fluidized paraffin. There was obtained an O/W type emulsion instead of the W/O type emulsion.

Table 2 shows the evaluated results of the obtained emulsion. The moisture retaining ratio was as shown in FIG. 5 (relative humidity of 20%) and in FIG. 6 (50° C. constant-temperature vessel).

Comparative Example 2

10 Grams of the emulsifier (S-4) and 190 g of a fluidized paraffin were introduced into a 300-ml beaker and were heated at 90° C. followed by stirring by using the T.K. homomixer at 2000 rpm for 5 minutes. After stirred, the mixture was deaerated and cooled for 2 hours in vacuum to obtain a fluidized paraffin suspension (labeled as LPS-X).

The fluidized paraffin suspension (LPS-X) was heated at 70° C. while being stirred by using the T.K. homomixer, and to which was added the solution S-5 little by little, such that LPS-X:solution S-5=70:30 (weight ratio). After stirred at 10,000 rpm for 10 minutes, the mixture was deaerated and cooled for 2 hours in vacuum to obtain a W/O type emulsion (content of the sum of the sample S-4 and the sample S-5, 4.4% by weight).

Table 2 shows the evaluated results of the obtained emulsion.

The emulsion exhibited favorable stability at room temperature, but was divided into phases in the 50° C. constant-temperature vessel. The emulsion further exhibited poor tint and emitted offensive odor.

Comparative Example 3

A W/O type emulsion (content of the sum of the sample S-4 and the sample S-5, 4.0% by weight) was obtained in the same manner as in Comparative Example 2 but by mixing the fluidized paraffin suspension LPS-X and the solution S-5 in such a manner that LPS-X:solution S-5=50:50 (weight ratio).

Table 2 shows the evaluated results of the obtained emulsion. The moisture retaining ratio was as shown in FIG. 5 (relative humidity of 20%) and in FIG. 6 (50° C. constant-temperature vessel).

The emulsion exhibited favorable stability at room temperature, but was divided into phases in the 50° C. constant-temperature vessel. The emulsion further exhibited poor tint and emitted offensive odor.

Comparative Example 4

An emulsion was prepared in the same manner as in Comparative Example 2 but by adding the fluidized paraffin suspension LPS-X and the solution S-5 in such a manner that LPS-X:solution S-5=30:70 (weight ratio). The emulsion has inverted into the O/W type from the W/O type, and the W/O type emulsion was not obtained.

Table 2 shows the evaluated results of the obtained W/O type emulsion. The moisture retaining ratio was as shown in FIG. 5 (relative humidity of 20%) and in FIG. 6 (50° C. constant-temperature vessel).

TABLE 2

| | Stability of W/O emulsion | | | | |
|---|---|---|---|---|---|
| | Room temperature, 7 days | 50° C., 7 days | Color | Odor | Electric conductivity ($\mu$S/cm) |
| Example 1 | ○ | ○ | white | no | — |
| Example 2 | ○ | ○ | white | no | — |
| Example 3 | ○ | ○ | white | no | 0.90 |
| Example 4 | ○ | ○ | white | no | 1.58 |
| Example 5 | ○ | ○ | white | no | 2.12 |
| Example 6 | ○ | ○ | white | no | 2.47 |
| Example 7 | ○ | ○ | white | no | 4.62 |
| Example 8 | ○ | ○ | pale yellow | no | 0.64 |
| Example 9 | ○ | ○ | white | no | 4.28 |
| Example 10 | ○ | ○ | white | no | 1.06 |
| Example 11 | ○ | ○ | white | no | 2.15 |
| Comparative Example 1 | — | — | white | no | 1136 |
| Comparative Example 2 | ○ | X | yellow | yes | 0.53 |
| Comparative Example 3 | ○ | X | pale yellow | yes | 2.97 |
| Comparative Example 4 | — | — | white | yes | 668 |

Example 12

One gram of the carboxylate of the Zn-type composite metal hydroxide of the sample S-1 was added to 50 ml of the fluidized paraffin, and the mixture was shaken, and was left to stand still to measure the swelling property (sedimented volume) to be 8.5 ml.

For the purpose of comparison, a carboxylate of the Mg-type composite metal hydroxide without at all containing Zn was measured for its swelling property. The sedimented volume was 5.5 ml. From this fact, it was learned that the carboxylate of the Zn-type composite metal hydroxide possessed the swelling property that was improved by more than 50%.

Example 13

15 Grams of the active terra abla and 2 g of the carboxylate of the Zn-type composite metal hydroxide of the sample S-1 were added to 100 ml of the fluidized paraffin to measure the dispersion stability (sedimented property). The sedimented volume after 24 hours have passed was 70.0 ml.

For the purpose of comparison, a carboxylate of the Mg-type composite metal hydroxide without at all containing Zn was measured for its swelling property. The sedimented volume was 46.5 ml. The organic bentonite of the sample S-4 was also measured to find that the sedimented volume was 41.5 ml.

From this fact, it was learned that the carboxylate of the Zn-type composite metal hydroxide exhibits excellent dispersion stability.

Example 14

30 Grams of the carboxylate of the Zn-type composite metal hydroxide of the sample (S-1) was added to 170 g of the fluidized paraffin to measure the thixotropic property to be 6.7 (up) and 6.3 (down).

For the purpose of comparison, a carboxylate of the Mg-type composite metal hydroxide without at all containing Zn was measured for its thixotropic property to be 3.4 (up) and 3.1 (down).

From this fact, it was learned that the carboxylate of the Zn-type composite metal hydroxide exhibits excellent thixotropic property.

What is claimed is:

1. An oiliness agent comprising a carboxylate of a composite metal hydroxide having a chemical composition represented by the following general formula (1), $$M^2{}_a M^3{}_x(OH)_y(A)_z \cdot nH_2O \tag{1}$$

wherein
 $M^2$ indicates a divalent metal,
 $M^3$ indicates a trivalent metal,
 A indicates an anion of an aliphatic carboxylic acid,
 a, x, y and z are numbers satisfying the following formulas:

a>0, $3x+2a-y-mz=0$ (wherein m is a valency of anion A), $0.3 \leq a/x \leq =2.5$ $1.5 \leq y/(a+x) \leq 3.0$ $1.0 \leq (a+x)/z \leq 20.0$, and n is a number of not larger than 7
wherein the carboxylate of the composite metal hydroxide has a diffraction peak at 2θ=1 to 2.5° in the X-ray diffraction (Cu-kα).

2. A thixotropy-imparting agent comprising an oiliness agent of claim 1.

3. A viscosity-imparting agent comprising an oiliness agent of claim 1.

4. A water-in-oil emulsion containing the oiliness agent of claim 1 as an emulsifier.

5. A water-in-oil emulsion according to claim 4, containing the carboxylate of the composite metal hydroxide in an amount of from 0.1 to 25% by weight.

6. A water-in-oil emulsion according to claim 4, wherein the divalent metal $M^2$ includes Mg and Zn, and the trivalent metal $M^3$ is Al.

7. A water-in-oil emulsion according to claim 4, which is obtained by adding the carboxylate of the composite metal hydroxide to an oil phase which is then mixed with an aqueous phase with stirring.

8. A base material for cosmetics comprising a water-in-oil emulsion of claim 4.

9. A water-in-oil emulsion according to claim 4, wherein a trioctahedral clay mineral is further contained as the emulsifier.

10. A water-in-oil emulsion according to claim 9, wherein the carboxylate of the composite metal hydroxide and the trioctahedral clay mineral are contained at a weight ratio of from 99.9:0.1 to 35:65 and in a total amount of from 0.1 to 25% by weight.

11. A water-in-oil emulsion according to claim 9, wherein the trioctahedral clay mineral is a stevensite clay mineral.

12. A water-in-oil emulsion according to claim 9, wherein the trioctahedral clay mineral is a sodium magnesium phillocilicate which substantially consists of magnesium, sodium and a silicon component only, and has an X-ray diffraction peak in a spacing of from 16 to 26 angstroms in a state of being treated with an ethylene glycol.

13. A water-in-oil emulsion according to claim 9, wherein the oil and water are present at a weight ratio in a range of from 99.9:0.1 to 8:92.

14. An oiliness agent comprising a carboxylate of a composite metal hydroxide having a chemical composition represented by the following general formula (1), $$M^2{}_a M^3{}_x(OH)_y(A)_z \cdot nH_2O \tag{1}$$

wherein
 $M^2$ indicates a divalent metal,
 $M^3$ indicates a trivalent metal,
 A indicates an anion of an aliphatic carboxylic acid,
 a, x, y and z are numbers satisfying the following formulas:

a>0, $3x+2a-y-mz=0$ (wherein m is a valency of anion A), $0.3<a/x<2.5$ $1.5<y/(a+x)<3.0$ $1.0<(a+x)/z<20.0$, and n is a number of not larger than 7, wherein at least part of the divalent metal $M^2$ is zinc in the carboxylate of the composite metal hydroxide.

15. An oiliness agent comprising a carboxylate of a composite metal hydroxide having a chemical composition expressed by the following general formula (1a)

$$(Zn)_p(Q)_q M^3{}_x(OH)_y(A)_z \cdot nH_2O \tag{1a}$$

wherein,
 $M^3$, A, b, x, y and z
 $M^3$ indicates a trivalent metal,
 A indicates an anion of an aliphatic carboxylic acid,
 x, y and z are numbers satisfying the following formulas:

$(p+q)>0$, $3x+2(p+q)-y-mz=0$ (wherein m is a valency of anion A), $0.3<(p+g)/x<2.5$ $1.5<y/((p+q)+x)<3.0$ $1.0<((p+g)+x)/z<20.0$, and n is a number of not larger than 7
 Q indicates a divalent metal other than Zn, and
 p/(p+q)>0.1.

16. An oiliness agent according to claim 15, wherein the divalent metal is Mg.

17. An oiliness agent according to claim 15, wherein the trivalent metal is Al.

18. A thixotropy-imparting agent comprising an oiliness agent of claim 15.

19. A viscosity-imparting agent comprising an oiliness agent of claim 15.

* * * * *